US011002740B2

(12) United States Patent
Jacobelli et al.

(10) Patent No.: US 11,002,740 B2
(45) Date of Patent: May 11, 2021

(54) METHODS OF DETECTING AND REDUCING CANCER CELL CENTRAL NERVOUS SYSTEM COLONIZATION (71) Applicant: National Jewish Health, Denver, CO (US)

(72) Inventors: Jordan Jacobelli, Denver, CO (US); Scott Thompson, Denver, CO (US); Jeffrey Chung, Boulder, CO (US)

(73) Assignee: National Jewish Health, Denver, CO (US)

( * ) Notice: Subject to any disclaimer, the term of this patent is extended or adjusted under 35 U.S.C. 154(b) by 232 days.

(21) Appl. No.: 16/023,650

(22) Filed: Jun. 29, 2018

(65) Prior Publication Data
US 2019/0004053 A1 Jan. 3, 2019

Related U.S. Application Data (60) Provisional application No. 62/527,798, filed on Jun. 30, 2017.

(51) Int. Cl.
| | |
|---|---|
| *G01N 33/574* | (2006.01) |
| *A61P 35/02* | (2006.01) |
| *C07K 16/30* | (2006.01) |
| *A61K 45/06* | (2006.01) |
| *A61K 39/395* | (2006.01) |
| *C12Q 1/6886* | (2018.01) |
| *C12N 15/113* | (2010.01) |
| *A61K 31/573* | (2006.01) |
| *A61K 31/713* | (2006.01) |
| *A61K 31/506* | (2006.01) |
| *A61K 39/00* | (2006.01) |

(52) U.S. Cl.
CPC ..... *G01N 33/57496* (2013.01); *A61K 31/506* (2013.01); *A61K 31/573* (2013.01); *A61K 31/713* (2013.01); *A61K 39/39558* (2013.01); *A61K 45/06* (2013.01); *A61P 35/02* (2018.01); *C07K 16/3069* (2013.01); *C12N 15/1135* (2013.01); *C12Q 1/6886* (2013.01); *G01N 33/57426* (2013.01); *A61K 2039/804* (2018.08); *C07K 2317/21* (2013.01); *C07K 2317/76* (2013.01); *C12N 15/1138* (2013.01); *C12N 2310/14* (2013.01); *C12N 2320/31* (2013.01); *C12Q 2600/106* (2013.01); *C12Q 2600/112* (2013.01); *C12Q 2600/158* (2013.01); *G01N 2333/4727* (2013.01)

(58) Field of Classification Search
None
See application file for complete search history.

(56) References Cited

U.S. PATENT DOCUMENTS

| | | |
|---|---|---|
| 9,417,244 B2 | 8/2016 | Maheswaran et al. |
| 2004/0018513 A1 | 1/2004 | Downing et al. |
| 2005/0037439 A1 | 2/2005 | Bourner et al. |
| 2008/0095764 A1 | 4/2008 | Parsons et al. |
| 2014/0148354 A1 | 5/2014 | Campana et al. |

FOREIGN PATENT DOCUMENTS

| | | |
|---|---|---|
| WO | WO 2006/009915 | 1/2006 |
| WO | WO 2018/106660 | 6/2018 |

OTHER PUBLICATIONS

Stancovski et al. (PNAS, 88: 8691-8695, 1991).*
Jiang et al. (J. Biol. Chem., 280: 4656-4662, 2005).*
International Preliminary Report on Patentability for International (PCT) Patent Application No. PCT/US2018/040375, dated Jan. 9, 2020 8 pages.
Aragon-Ching et al. "CNS Metastasis: An Old Problem in a New Guise," Clinical Cancer Research, Mar. 2007, vol. 13, No. 6, pp. 1644-1647.
Boulos et al. "Chemotherapeutic agents circumvent emergence of dasatinib-resistant BCR-ABL kinase mutations in a precise mouse model of Philadelphia chromosome-positive acute lymphoblastic leukemia," Blood, Mar. 2011, vol. 117, No. 13, pp. 3585-3595.
Goshen et al. "High Incidence of Meningioma in Cranial Irradiated Survivors of Childhood Acute Lymphoblastic Leukemia," Pediatric Blood & Cancer, 2007, vol. 49, pp. 294-297.
Jacobelli et al. "Myosin-IIA and ICAM-1 Regulate the Interchange between Two Distinct Modes of T Cell Migration," The Journal of Immunology, Feb. 2009, vol. 182, No. 4, pp. 2041-2050.
Jacoby et al. "Murine models of acute leukemia: important tools in current pediatric leukemia research," Frontiers in Oncology, May 2014, vol. 4, article 95, 14 pages.
Moore et al. "Cognitive Consequences and Central Nervous System Injury Following Treatment for Childhood Leukemia," Seminars in Oncology Nursing, Nov. 2000, vol. 16, No. 4, pp. 279-290.
Pui et al. "Current management and challenges of malignant disease in the CNS in paediatric leukaemia," The Lancet Oncology, Mar. 2008, vol. 9, No. 3, pp. 257-268.
Pui et al. "Central Nervous System Disease in Hematological Malignancies: Historical Perspective and Practical Applications," Seminars in Oncology, Aug. 2009, vol. 36, Suppl 2, pp. S2-S16.
Shuper et al. "Methotrexate Treatment Protocols and the Central Nervous System: Significant Cure With Significant Neurotoxicity," Journal of Child Neurology, Sep. 2000, vol. 15, No. 9, pp. 573-580.
Silveira et al. "Gene expression pattern contributing to prognostic factors in childhood acute lymphoblastic leukemia," Leukemia & Lymphoma, Feb. 2013, vol. 54, No. 2, pp. 310-314.
Strehl et al. "Characterization of Two Novel Protocadherins (PCDH8 and PCDH9) Localized on Human Chromosome 13 and Mouse Chromosome 14," Genomics, 1998, vol. 53, pp. 81-89.
Wigton et al. "Myosin-IILLA regulates leukemia engraftment and brain infiltration in a mouse model of acute lymphoblastic leukemia," Journal of Leukocyte Biology, Jul. 2016, vol. 100, pp. 143-153.

(Continued)

*Primary Examiner* — Nelson B Moseley, II
(74) *Attorney, Agent, or Firm* — Sheridan Ross P.C.

(57) ABSTRACT

The present invention is related to novel methods for detecting and reducing cancer cell central nervous system colonization and methods of treating subjects having cancers that colonize in the central nervous system.

10 Claims, 6 Drawing Sheets

(56) References Cited

OTHER PUBLICATIONS

Wolff et al. "The CNS is a sanctuary for leukemic cells in mice receiving imatinib mesylate for Bcr/Abl-induced leukemia," Blood, Jun. 2003, vol. 101, No. 12, pp. 5010-5013.
International Search Report and Written Opinion for International (PCT) Patent Application No. PCT/US2018/040375, dated Sep. 24, 2018 9 pages.

* cited by examiner

METHODS OF DETECTING AND REDUCING CANCER CELL CENTRAL NERVOUS SYSTEM COLONIZATION

CROSS-REFERENCE TO RELATED APPLICATIONS

This application claims the benefit of priority under 35 U.S.C. § 119(e) to U.S. Provisional Patent Application No. 62/527,798, filed Jun. 30, 2017. The entire disclosure of U.S. Provisional Patent Application No. 62/527,798 is incorporated herein by reference.

BACKGROUND OF THE INVENTION

Acute lymphoblastic Leukemia (ALL) is the most common type of childhood cancer with approximately 3000 newly diagnosed children each year in the USA. Current ALL therapies lead to high remission rates, but a significant number of patients relapse, with the relapsing leukemia often involving the Central Nervous System (CNS) (Pfeifer, H. et al. Risk and prognosis of central nervous system leukemia in patients with Philadelphia chromosome-positive acute leukemias treated with imatinib mesylate. *Clinical cancer research: an official journal of the American Association for Cancer Research* 9, 4674-4681 (2003); Leis, J. F. et al. Central nervous system failure in patients with chronic myelogenous leukemia lymphoid blast crisis and Philadelphia chromosome positive acute lymphoblastic leukemia treated with imatinib (STI-571). *Leukemia & lymphoma* 45, 695-698 (2004); Pui, C. H. & Thiel, E. Central nervous system disease in hematologic malignancies: historical perspective and practical applications. *Seminars in oncology* 36, S2-S16 (2009)). The CNS acts as a 'sanctuary' site due to the presence of the blood brain barrier, which shields hematological cancer cells (such as leukemia cells and lymphoma cells) from treatments including tyrosine kinase inhibitors (TKIs) and chemotherapy (Aragon-Ching, J. B. & Zujewski, J. A. CNS metastasis: an old problem in a new guise. *Clinical cancer research: an official journal of the American Association for Cancer Research* 13, 1644-1647 (2007); Wolff, N.C., Richardson, J. A., Egorin, M. & Ilaria, R. L., Jr. The CNS is a sanctuary for leukemic cells in mice receiving imatinib mesylate for Bcr/Abl-induced leukemia. *Blood* 101, 5010-5013 (2003)). In the case of pediatric ALL only ~5% of patients are initially diagnosed with CNS involvement; however, in the absence of CNS-directed treatments up to 40% of relapses can have CNS involvement (Pui, C. H. & Thiel, E. Central nervous system disease in hematologic malignancies: historical perspective and practical applications. *Seminars in oncology* 36, S2-S16 (2009); Pui, C.-H. & Howard, S. C. Current management and challenges of malignant disease in the CNS in paediatric leukaemia. *The Lancet Oncology* 9, 257-268 (2008)). Even though in some cases the leukemia may already be present in the CNS below detection levels, in many cases the leukemia does not initially involve the CNS and can infiltrate the CNS during or after treatment. Additional treatments such as cranial irradiation, intrathecal administration of chemotherapy, or high dose chemotherapy have been used to reduce CNS relapses. With these CNS-specific treatments, the relapse rate can be lowered to 5-15% depending on the type and intensity of the treatments (Pui, C. H. & Thiel, E. Central nervous system disease in hematologic malignancies: historical perspective and practical applications. *Seminars in oncology* 36, S2-S16 (2009); Pui, C.-H. & Howard, S. C. Current management and challenges of malignant disease in the CNS in paediatric leukaemia. *The Lancet Oncology* 9, 257-268 (2008)). However, short- and long-term side-effects, such as acute neurotoxicity, brain cancer, cognitive impairment and learning disabilities, can be very severe, particularly in children (Goshen, Y. et al. High incidence of meningioma in cranial irradiated survivors of childhood acute lymphoblastic leukemia. *Pediatric blood & cancer* 49, 294-297 (2007); Shuper, A. et al. Methotrexate treatment protocols and the central nervous system: significant cure with significant neurotoxicity. *Journal of child neurology* 15, 573-580 (2000); Moore, I. M. et al. Cognitive consequences and central nervous system injury following treatment for childhood leukemia. *Seminars in oncology nursing* 16, 279-290; discussion 291-279 (2000)).

Thus, interventions that prevent or reverse hematological cancer cell (including leukemia and/or lymphoma cell) colonization of the CNS, and that can be combined with standard therapies, are novel tools to achieve full remission and improve long-term survival while reducing the severe side effects of CNS-directed treatments. There is an unmet need in the art to inhibit or reverse hematological cancer cell infiltration and colonization of the CNS, which can be present at diagnosis or happen over the course of anti-cancer treatments, in order to prevent relapses.

SUMMARY OF THE INVENTION

One embodiment of the present invention is a method of treating cancer comprising administering to a subject in need thereof, a PCDH9 inhibitor. In one aspect, the cancer is leukemia or lymphoma. In still another aspect, the leukemia is Acute Lymphoblastic Leukemia (ALL) or Acute Myeloid Leukemia (AML).

Another embodiment of the present invention is a method to identify a subject at risk for leukemia cell colonization of the central nervous system (CNS) in a subject having leukemia, the method comprising (a) obtaining a blood sample from the subject; (b) detecting the expression level of PCDH9 in the sample; and (c) identifying the subject as at risk for leukemia cell colonization of the CNS when either the presence of PCDH9 expression is detected above a control threshold level or the expression level of PCDH9 in the sample is higher than the expression level of PCHD9 from a control.

Still another embodiment of the present invention is a method to reduce leukemia relapse in a subject, comprising (a) obtaining a blood sample from the subject; (b) detecting the expression level of PCDH9 in the sample; (c) identifying the subject as at risk for leukemia relapse when either the presence of PCDH9 expression is detected above a control threshold level or the expression level of PCDH9 in the sample is higher than the expression level of PCHD9 from a control; and (d) administering a PCDH9 inhibitor to the subject at risk.

Another embodiment method to inhibit or reverse leukemia cell colonization of the CNS in a subject comprising (a) obtaining a blood sample from the subject; (b) detecting the expression level of PCDH9 in the sample; (c) identifying the subject as at risk for leukemia cell colonization of the CNS when either the presence of PCDH9 expression is detected above a control threshold level or the expression level of PCDH9 in the sample is higher than the expression level of PCHD9 from a control; and (d) administering a PCDH9 inhibitor to the subject.

In any of the embodiments of the invention described above or elsewhere herein, the PCDH9 inhibitor is selected from the group consisting of an antibody, an antisense molecule, an siRNA molecule, an shRNA molecule, a receptor antagonist, a chemical entity, a nucleotide, a peptide, and a protein. In one aspect, the PCDH9 inhibitor is an PCDH9 antibody.

In any of the embodiments of the invention described above or elsewhere herein, the subject is further administered a systemic therapy selected from the group consisting of chemotherapy, radiation, and tyrosine kinase inhibitor (TKI) therapy.

BRIEF DESCRIPTION OF THE DRAWINGS

FIGS. 1A and 1B. Differential phenotype of systemic B-cell acute lymphoblastic leukemia (B-ALL) and CNS B-ALL after in vivo transfer. $5 \times 10^4$ systemic B-ALL cells or CNS B-ALL cells were transferred into recipient mice and scored daily for signs of leukemia and CNS pathology. FIG. 1A: Quantification of spleen weight at the time of death of recipient mice transferred with either CNS or systemic B-ALL cells. Black line indicates normal spleen weight. FIG. 1B: Quantification of CNS pathology in recipient mice transferred with CNS or systemic B-ALL cells. CNS pathology scoring: limp tail=1; limp tail and partial hind limb paralysis=2; limp tail and full hind limb paralysis=3; limp tail, complete hind leg and partial front leg paralysis=4. Data are pooled from 2 independent experiments with cohorts of 5 mice/group/experiment; error bars are SEM.

FIG. 4A: Incidence of CNS pathology (p=0.0059). FIG. 4B: Quantification of severity of CNS pathology in recipient mice (p<0.0001). Data are pooled from 2 experiments with cohorts of 5 mice/group/experiment; error bars are SEM.

FIG. 7A: Incidence of CNS pathology (p=0.0059). FIG. 7B: Quantification of severity of CNS pathology in recipient mice (p<0.0001). Data are pooled from 3 experiments with cohorts of 4-5 mice/group/experiment; error bars are SEM.

DETAILED DESCRIPTION OF INVENTION

Acute lymphoblastic Leukemia (ALL) is the most common childhood cancer. Current therapies achieve high remission rates, but a significant number of patients relapse, often with Central Nervous System (CNS) involvement. Some CNS-directed treatments reduce CNS relapses but do not eliminate them. CNS-directed treatments such as cranial irradiation, intrathecal administration of chemotherapy, or high dose chemotherapy have been used to reduce CNS relapses. While the relapse rate has been significantly lowered, particularly with some high-intensity CNS-specific treatments, it has not been completely eliminated. Additionally, short- and long-term side-effects of CNS-directed treatments, such as acute neurotoxicity, brain cancer, cognitive impairment and learning disabilities, can be very severe particularly in children. Given these serious side-effects of current CNS-directed therapies in pediatric patients, inhibiting CNS colonization of leukemia cells is a valuable tool to reduce leukemia relapse, and improve survival and the quality of life in ALL patients by eliminating or reducing harmful CNS-directed therapies. Thus, methods to inhibit hematological cancer cell (including leukemia cells and lymphoma cells) colonization of the CNS to prevent relapses as disclosed herein fulfil an unmet need in the art.

As disclosed herein, targets that enable leukemia cell colonization of the CNS have been identified by comparing leukemia cells that colonize the CNS versus leukemia cells that do not. This analysis identified Protocadherin-9 (PCDH9) as an ectopically expressed protein in CNS-colonizing leukemia cells. Based on this data, ectopic expression of PCDH9 can enable leukemia cells to colonize the CNS and give rise to CNS pathology and relapses. Thus, determining the efficacy of targeting PCDH9 to prevent or reverse leukemia cell colonization of the CNS and improve long-term survival by reducing relapses fulfills an unmet need in the art. Instead of using toxic treatments (such as intrathecal chemotherapy or radiation) to kill the leukemia cells in the CNS, the inventors demonstrate that inhibiting leukemia cell colonization of the CNS by inhibiting PCDH9 is an effective alternative. In addition to validating PCDH9 as a novel target for leukemia treatment, PCDH9 is a new diagnostic target that can establish the risk for CNS colonization in leukemia patients. This allows more effective stratification of CNS treatments, thereby reducing the use and intensity of deleterious CNS-directed therapies in lower risk patients including pediatric patients and thus improving their quality of life.

Figure 1A:
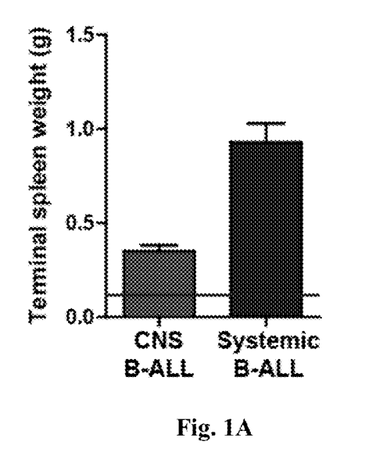
Figure 1B:
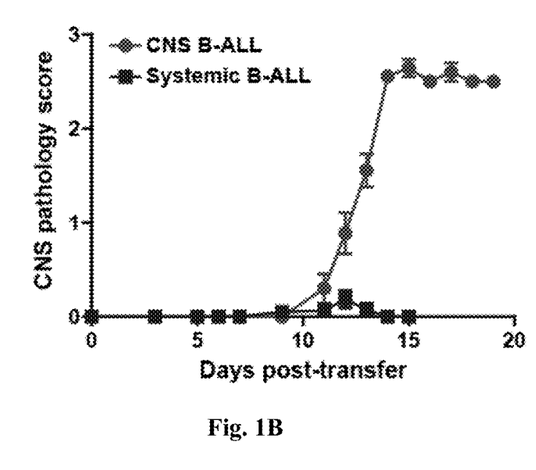

To disseminate into the CNS, hematological cancer cells, such as leukemia cells or lymphoma cells, exit the blood circulation by migrating across blood vessel walls. Once in the CNS, these cells can establish a niche, escape systemic anti-cancer treatments, and eventually give rise to CNS relapses. The mechanisms of leukemia cell entry and colonization of the CNS are mostly unknown. Using mouse and human models of pre-B cell ALL (B-ALL), factors that allow leukemia cells to enter and colonize the CNS have been determined. The gene expression profile of two similarly derived mouse B-ALL cell lines that have very different CNS colonization phenotypes were compared. The first ALL cell line has a typical 'systemic' phenotype of bone marrow and spleen involvement, while the second B-ALL cell line rapidly disseminates to the CNS and gives rise to CNS pathology (ascending paralysis of the recipient mice) (FIG. 1—pathology scoring). RNA sequencing analysis revealed that the most differentially expressed gene was PCDH9.

Figure 2:
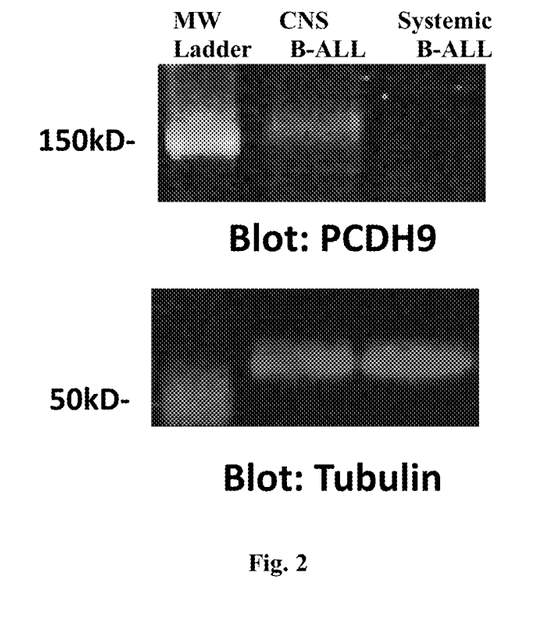
FIG. 2. PCDH9 is expressed in CNS leukemia cells but not systemic leukemia cells. Western blot analysis showing protein expression of PCDH9 in CNS B-ALL cells and lack of protein expression in systemic B-ALL cells.
Figure 4A:
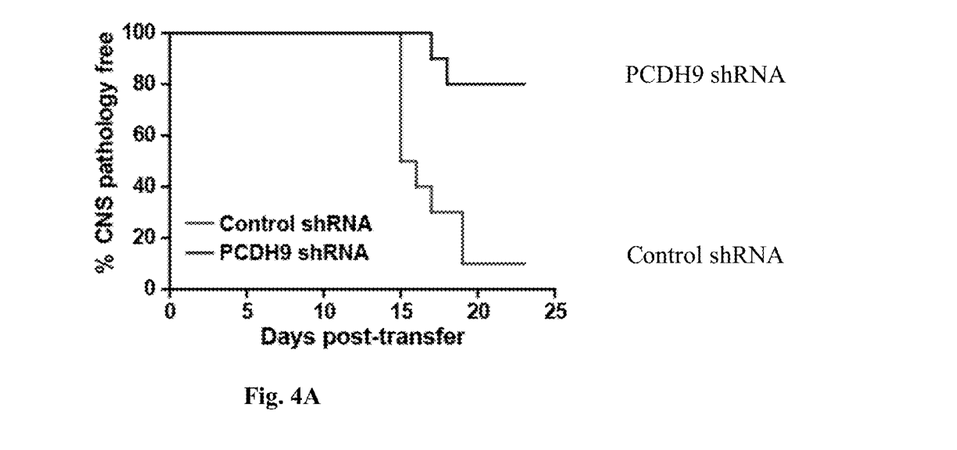
FIGS. 4A and 4B. PCDH9 depletion in B-ALL cells greatly reduces the incidence and severity of CNS pathology. $5 \times 10^4$ control or PCDH9 KD (knock-down) CNS B-ALL cells were transferred into recipient mice and scored daily for signs of leukemia and CNS pathology (as described in FIG. 1).
Figure 4B:
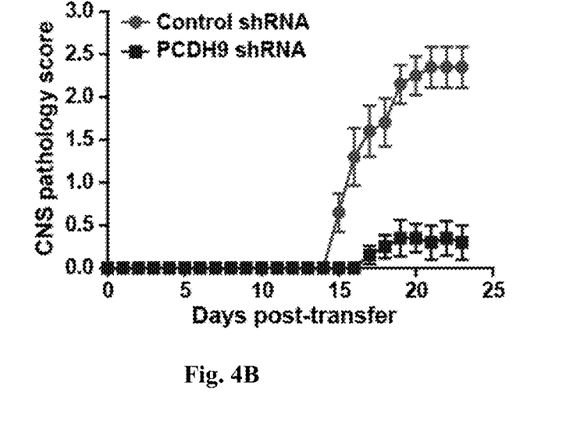

PCDH9 is a transmembrane adhesion receptor of the protocadherin family, which is known to mediate calcium-dependent cell adhesion in neuronal tissues (Strehl, S., Glatt, K., Liu, Q. M., Glatt, H. & Lalande, M. Characterization of two novel protocadherins (PCDH8 and PCDH9) localized on human chromosome 13 and mouse chromosome 14. *Genomics* 53, 81-89 (1998)). PCDH9 was virtually absent in the B-ALL line that exhibited a systemic phenotype, and was highly expressed (>27-fold) in the B-ALL line with the CNS colonization phenotype by both mRNA and Western Blot analysis (Table 1, FIG. 2). PCDH9 is not expressed in normal leukocytes, but gene profiling of leukemia patient samples available in public databases shows that PCDH9 is ectopically expressed in various human leukemia samples. PCDH9 upregulation is also a poor prognostic factor in ALL (Silveira, V. S. et al. Gene expression pattern contributing to prognostic factors in childhood acute lymphoblastic leukemia. *Leukemia & lymphoma* 54, 310-314 (2013)). PCDH9 depletion in leukemia cells greatly reduces their ability to give rise to CNS pathology (FIG. 4). Based on these data, ectopic expression of PCDH9 in leukemia cells is expected to enable leukemia cells to colonize the CNS and cause CNS pathology and relapses. Both the mouse ALL model just described and a human ALL xenograft model that also gives rise to CNS pathology in recipient mice can be used.

TABLE 1

Comparison of PCDH9 mRNA expression in systemic vs. CNS leukemia cells

| | 'Systemic' B-ALL average (reads/10$^6$) | 'CNS' B-ALL average (reads/10$^6$) | Normalized fold change (DSeq2) | Adjusted p value |
|---|---|---|---|---|
| PCDH-9 | 0.5 | 1965.3 | 27.48 | 1.5732 × 10$^{-58}$ |

RNA sequencing was performed on the systemic and CNS B-ALL cells and analyzed using the D SEQ2 software. The most highly differentially expressed gene between the two leukemia lines was PCDH9.

The role of PCDH9 in allowing leukemia cells to enter and colonize the CNS, and give rise to CNS pathology and relapse is demonstrated herein. Furthermore, the results provide target validation for PCDH9 as a novel point of therapeutic intervention to inhibit leukemia cell colonization of the CNS and prevent relapses, including as part of combination therapies. Given the serious side-effects of CNS-directed therapies in children, inhibiting CNS colonization of leukemia cells is a valuable tool to improve current therapies by decreasing relapses following TKI and chemotherapy while also reducing the need or intensity of CNS-directed therapies.

Leukemia as well as lymphoma cell colonization of the CNS can be particularly problematic since the CNS acts as 'sanctuary' site that protects leukemia or lymphoma cells from systemic treatments including chemotherapy and TKIs. This is mainly due to the reduced permeability of these drugs through the blood-brain barrier (Aragon-Ching, J. B. & Zujewski, J. A. CNS metastasis: an old problem in a new guise. *Clinical cancer research: an official journal of the American Association for Cancer Research* 13, 1644-1647 (2007); Wolff, N. C., Richardson, J. A., Egorin, M. & Ilaria, R. L., Jr. The CNS is a sanctuary for leukemic cells in mice receiving imatinib mesylate for Bcr/Abl-induced leukemia. *Blood* 101, 5010-5013 (2003)). Thus, therapeutics that inhibit leukemia and/or lymphoma cell colonization of the CNS can be used, in combination with systemic TKIs and/or chemotherapy, to more completely eradicate leukemia, to prevent relapses, and thereby increase long-term survival (typically defined as longer than 5 years from diagnosis in the case of ALL). Furthermore, reducing the need, frequency and intensity of treatments such as intrathecal chemotherapy can significantly reduce the deleterious side-effects of these therapies especially in children.

Identification of PCDH9 as a novel target for prevention of leukemia CNS relapses: Relatively little is known about PCDH9. It belongs to the protocadherin family, a group of transmembrane proteins that mediate Ca$^{2+}$-dependent homotypic cell adhesion. PCDH9 is predominantly expressed in neuronal tissues and not normally expressed in leukocytes (Strehl, S., Glatt, K., Liu, Q. M., Glatt, H. & Lalande, M. Characterization of two novel protocadherins (PCDH8 and PCDH9) localized on human chromosome 13 and mouse chromosome 14. *Genomics* 53, 81-89 (1998)). Ectopic expression of PCDH9 in human leukemia cells has been demonstrated by expression profiling, and includes but is not limited to human ALL. Furthermore, PCDH9 expression is a poor prognostic factor in ALL (Silveira, V. S. et al. Gene expression pattern contributing to prognostic factors in childhood acute lymphoblastic leukemia. Leukemia & lymphoma 54, 310-314 (2013)). Ectopic expression of PCDH9 in leukemia cells is believed to allow them to adhere and interact with neuronal and/or glial cells enabling the leukemia cells to establish a niche in the CNS.

Use of PCDH9 as a new diagnostic tool to predict the risk of CNS colonization: PCDH9 expression in leukemia cells is a factor that enables leukemia cells to colonize the CNS which allows for staining leukemia cells from a patient's blood sample for PCDH9 expression. This is a novel and greatly improved method to establish the risk for CNS colonization in leukemia patients. This enables more effective treatment stratification, thereby reducing the need and intensity of harmful CNS-directed therapies in lower risk patients.

As discussed in the Example Section below, a mouse ALL model and a human ALL xenograft model that both give rise to CNS pathology are used to compare the ability of control ALL cells and PCDH9-depleted ALL cells to colonize the CNS and induce CNS pathology.

PCDH9 expression in leukemia cells enables their establishment in the CNS. Using the CNS B-ALL cells in a mouse ALL transfer model, the ability of control shRNA and PCDH9 shRNA (PCDH9 KD) B-ALL cells to infiltrate the CNS and give rise to CNS pathology by time-course analysis is compared. Furthermore, using the human leukemia cell line NALM-6, knock-out (KO) of PCDH9 is shown to prevent CNS pathology by the human leukemia cells.

An established mouse B-ALL model (Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011); Williams, R. T., Roussel, M. F. & Sherr, C. J. Arf gene loss enhances oncogenicity and limits imatinib response in mouse models of Bcr-Abl-induced acute lymphoblastic leukemia. *Proceedings of the National Academy of Sciences of the United States of America* 103, 6688-6693 (2006); Williams, R. T., den Besten, W. & Sherr, C. J. Cytokine-dependent imatinib resistance in mouse BCR-ABL+, Arf-null lymphoblastic leukemia. *Genes & development* 21, 2283-2287 (2007)) is used in the example section herein. B-ALL are often initiated by a translocation between chromosomes 9 and 22, known as the Philadelphia chromosome, which results in the expression of the Bcr-Abl fusion protein. The presence of Bcr-Abl in leukemia cells typically carries a poor prognosis. Two mouse Bcr-Abl+ Arf–/– B-ALL cell lines were derived by transducing bone marrow cells from Arf–/– (a tumor suppressor) C57BL/6 mice with p185Bcr-Abl and co-expressing either a GFP or luciferase as a marker (Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011); Williams, R. T., Roussel, M. F. & Sherr, C. J. Arf gene loss enhances oncogenicity and limits imatinib response in mouse models of Bcr-Abl-induced acute lymphoblastic leukemia. *Proceedings of the National Academy of Sciences of the United States of America* 103, 6688-6693 (2006)). While both B-ALL lines consistently induce lymphoid leukemia in healthy non-irradiated mice, these two B-ALL cell lines were determined to have very different in vivo phenotypes. The luciferase-expressing B-ALL cell line gives rise to a typical 'systemic' phenotype of bone marrow and spleen involvement, while the GFP-expressing B-ALL cell line infiltrates the CNS and gives rise to CNS pathology (paralysis of the recipient mice) in addition to systemic dissemination (FIG. 1).

Figure 6:
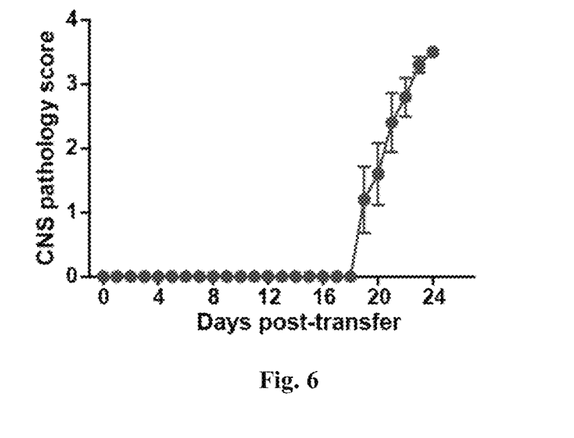
FIG. 6. NALM-6 leukemia cells cause CNS pathology. $10^6$ NALM-6 cells were transferred into severe combined immunodeficiency (SCID) recipient mice and scored daily for signs of leukemia and CNS pathology (as described in the text and FIG. 1). Quantification of severity of CNS pathology in recipient mice is shown.

To extend these results to human ALL, a xenograft model with the human pre-B cell ALL cell line NALM-6, which carries a (5; 12) translocation was used. NALM-6 cells reliably engraft in SCID mice and have been used to test anti-leukemia experimental therapies in vivo (Jacoby, E., Chien, C. D. & Fry, T. J. Murine models of acute leukemia: important tools in current pediatric leukemia research. *Frontiers in oncology* 4, 95 (2014)). Importantly, NALM-6 cells colonize the CNS at high frequency leading to CNS pathology in the recipient mice similarly to the mouse B-ALL model (Gunther, R. et al. Biotherapy for xenografted human central nervous system leukemia in mice with severe combined immunodeficiency using B43 (anti-CD19)-pokeweed antiviral protein immunotoxin. *Blood* 85, 2537-2545 (1995)) (FIG. 6).

Figure 5:
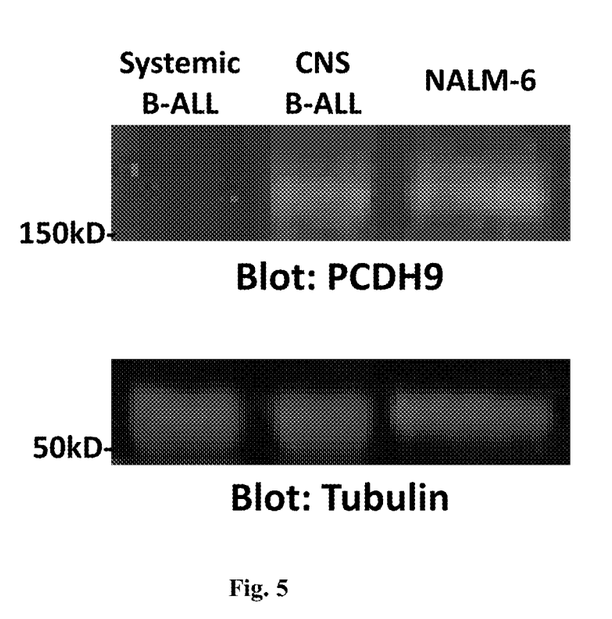
FIG. 5. PCDH9 is expressed in CNS B-ALL and in NALM-6 leukemia cells, but not systemic B-ALL cells. Western blot analysis showing protein expression of PCDH9 in CNS B-ALL and NALM-6 cells and lack of PCDH9 expression in systemic B-ALL cells.

Differential expression of PCDH9 in systemic vs. CNS leukemia cells. To determine the molecular causes for such different in vivo phenotypes of the two mouse B-ALL cell lines used herein, RNA sequencing analysis was done to investigate differences in the expression profile between these B-ALL cell lines. Analysis revealed that the most differentially expressed gene was PCDH9, which was virtually absent from the systemic B-ALL cells and highly expressed in the CNS B-ALL cells (>27-fold based on the DSeq2 software analysis which normalizes fold changes based on expression levels and variance) (Table 1 and FIG. 2). PCDH9 protein expression in NALM-6 ALL cells (FIG. 5) was also confirmed.

Figure 3:
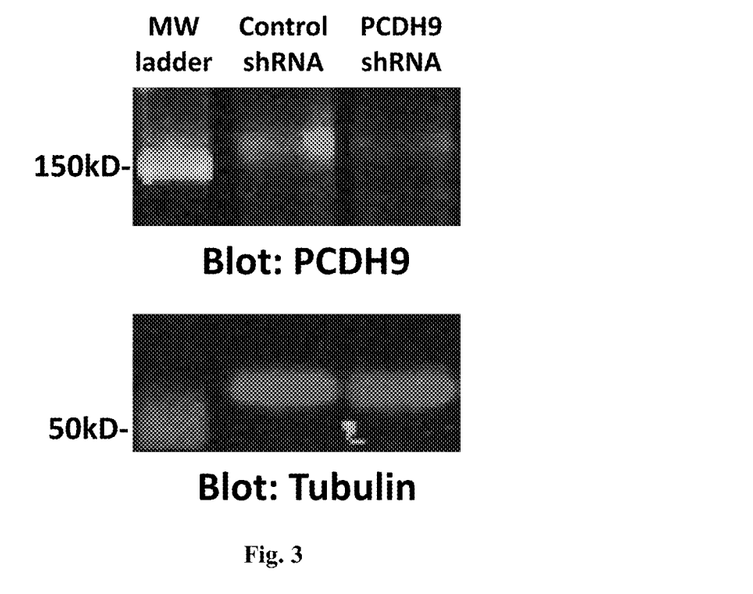
FIG. 3. shRNA-mediated depletion of PCDH9 in CNS leukemia cells. Western blot analysis showing PCDH9 protein levels in CNS B-ALL cells transduced with either control shRNA or PCDH9 specific shRNA.

Depletion of PCDH9 in leukemia cells: PCDH9 expression was knocked-down (KD) using an shRNA-mediated approach (FIG. 3). CNS B-ALL cells were transduced with control or PCDH9 inhibitory shRNA using retroviral vectors (pSiren-retroQ from Clontech), employing techniques similar to those used in other studies (Wigton, E. J., Thompson, S. B., Long, R. A. & Jacobelli, J. Myosin-IIA regulates leukemia engraftment and brain infiltration in a mouse model of acute lymphoblastic leukemia. *Journal of leukocyte biology* (2016); Jacobelli, J., Bennett, F. C., Pandurangi, P., Tooley, A. J. & Krummel, M. F. Myosin-IIA and ICAM-1 regulate the interchange between two distinct modes of T cell migration. *J Immunol* 182, 2041-2050 (2009)). Before use, the transduced cells were sorted based on the DsRed fluorescent marker co-expressed by the shRNA encoding retroviral vectors. To completely eliminate PCDH9 expression in the human NALM-6 cells, PCDH9 was knocked out using CRISPR/Cas9 technology.

PCDH9 depletion significantly reduces CNS pathology caused by B-ALL transfer: In experiments the in vivo effects of transferring CNS B-ALL cells transduced with either control shRNA or PCDH9 shRNA was compared. Even though, in the absence of anti-leukemia treatments, mice transferred with control or PCDH9 KD B-ALL cells eventually succumbed to the leukemia, the data showed that PCDH9 depletion in leukemia cells strongly reduced their ability to cause CNS pathology in the recipient mice (FIG. 4).

Figure 7A:
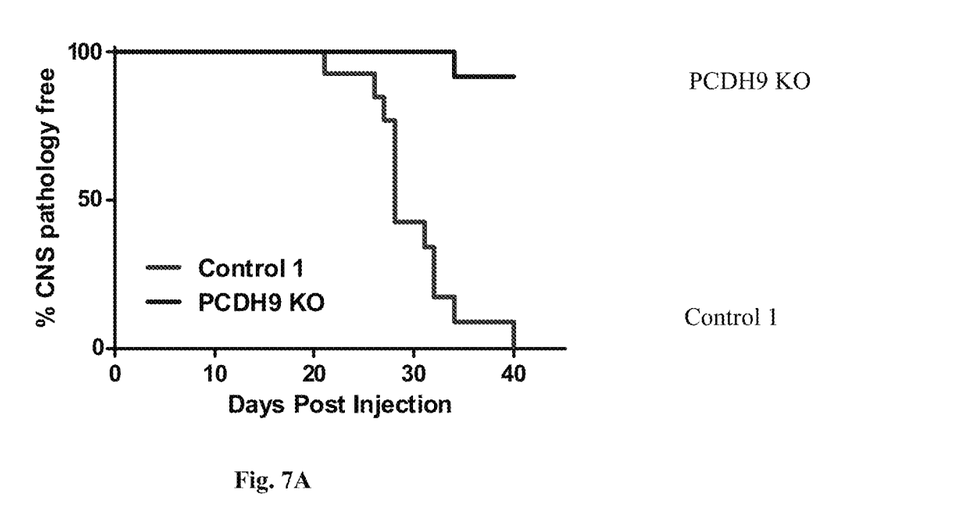
FIGS. 7A and 7B. PCDH9 KO (knock-out) in NALM-6 human leukemia cells greatly reduces the incidence and severity of CNS pathology. $5 \times 10^4$ control or PCDH9 KO NALM-6 cells were transferred into recipient mice and scored daily for signs of leukemia and CNS pathology.
Figure 7B:
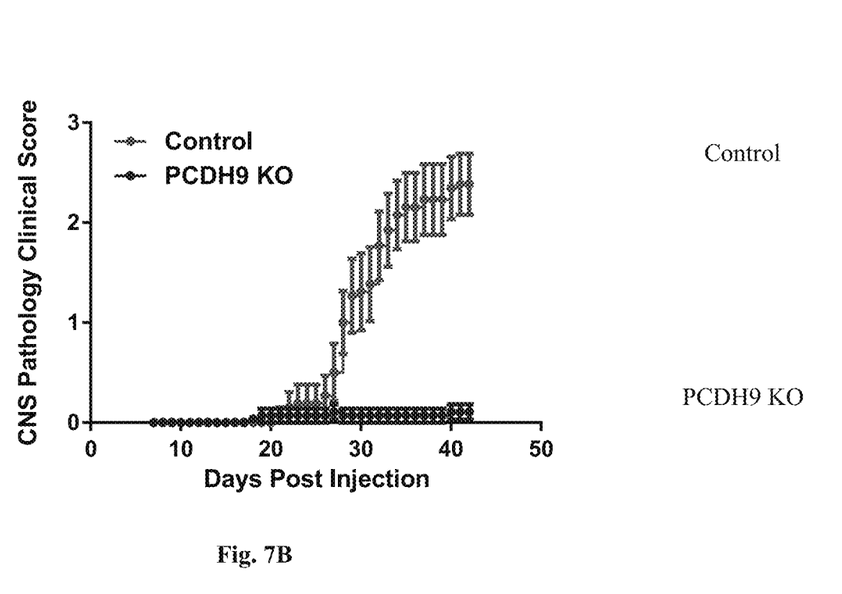

Knock-out of PCDH9 in human leukemia cells prevents CNS pathology: Control or PCDH9 KO human NALM-6 leukemia cells were transferred into SCID mice and leukemia progression and CNS pathology was monitored over time. These data showed that PCDH9 KO significantly reduced and almost eliminated the ability of NALM-6 cells to cause CNS pathology (FIG. 7). Overall, these data support that PCDH9 expression enables leukemia cells to colonize the CNS and cause CNS pathology.

Figure 8:
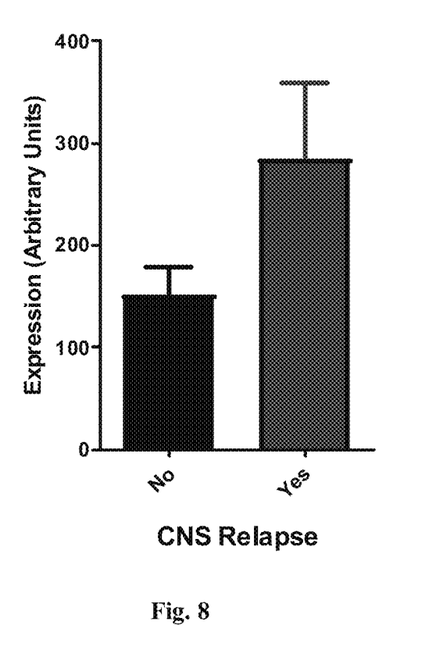
FIG. 8. Higher PCDH9 mRNA expression in ALL patients with CNS relapse. Patients were stratified between individuals that experienced a CNS relapse and those who did not. Expression of PCDH9 mRNA detected by microarray is shown. Results show that higher PCDH9 expression correlates with CNS relapse in ALL patients. (p=0.037)

Higher PCDH9 expression correlates with CNS relapse in ALL patients: PCDH9 expression was analyzed from publicly available microarray gene expression data from a clinical study of ALL patients. Comparing patients with or without CNS relapse suggests that PCDH9 expression is significantly higher in the patients with CNS relapse (FIG. 8).

By validating PCDH9 as a target in leukemia, new therapeutics to prevent or reverse leukemia colonization of the CNS 'sanctuary' site provide new treatment options for leukemia. Identifying PCDH9 as a protein that enables leukemia cells to colonize the CNS is used to develop new diagnostics to establish the risk for CNS dissemination in leukemia patients and more effectively stratify treatment.

One embodiment of the present invention is a method of treating cancer comprising administering to a subject in need thereof, a PCDH9 inhibitor. In one aspect, the cancer is a hematological cancer including but not limited to leukemia and/or lymphoma. In one aspect, the leukemia is Acute Lymphoblastic Leukemia (ALL) or Acute Myeloid Leukemia (AML). In one aspect of the invention described herein, the subject has been diagnosed as having cancer. In one aspect the cancer is a hematological cancer.

Another embodiment of the present invention is the use of a PCDH9 inhibitor for treating cancer in a subject. In one aspect, the cancer is a hematological cancer including but not limited to leukemia and/or lymphoma. In one aspect, the leukemia is Acute Lymphoblastic Leukemia (ALL) or Acute Myeloid Leukemia (AML). In one aspect of the invention described herein, the subject has been diagnosed as having cancer. In one aspect the cancer is a hematological cancer.

One embodiment of the present invention is a method to identify a subject at risk for hematological cancer cell colonization of the central nervous system (CNS) in a subject having been diagnosed as having the hematological cancer. The method comprising obtaining a sample from the subject; detecting the expression level of PCDH9 in the sample; and identifying the subject as at risk for hematological cancer cell colonization of the CNS when either the presence of PCDH9 expression is detected above a control threshold level or the expression level of PCDH9 in the sample is higher than the expression level of PCHD9 from a control. In one aspect, the hematological cancer is leukemia or lymphoma.

Still another embodiment of the present invention is a method to reduce hematological cancer relapse in a subject. The method comprises obtaining a sample from the subject; detecting the expression level of PCDH9 in the sample; identifying the subject as at risk for hematological cancer relapse when either the presence of PCDH9 expression is detected above a control threshold level or the expression level of PCDH9 in the sample is higher than the expression level of PCHD9 from a control; and administering a PCDH9 inhibitor to the subject at risk. In one aspect, the hematological cancer is leukemia or lymphoma.

Another embodiment of the present invention is the use of a PCDH9 inhibitor to reduce hematological cancer relapse in as subject.

Another embodiment of the present invention is a method to inhibit or reverse hematological cancer cell colonization of the CNS in a subject. The method comprises obtaining a sample from the subject; detecting the expression level of PCDH9 in the sample; identifying the subject as at risk for hematological cancer cell colonization of the CNS when either the presence of PCDH9 expression is detected above a control threshold level or the expression level of PCDH9 in the sample is higher than the expression level of PCDH9 from a control; and administering a PCDH9 inhibitor to the subject. In one aspect, the hematological cancer is leukemia or lymphoma.

Another embodiment of the present invention is the use of a PCDH9 inhibitor to inhibit or reduce hematological cancer cell colonization of the CNS in a subject.

A patient or subject sample can include any bodily fluid or tissue from a patient that may contain the RNA or protein encoded by the genes contemplated here. The term "sample" or "patient sample" or "subject sample" can be used generally to refer to a sample of any type which contains products that are to be evaluated by the present method, including but not limited to, a sample of isolated cells, a tissue sample and/or a bodily fluid sample. According to the present invention, a sample of isolated cells is a specimen of cells, typically in suspension or separated from connective tissue which may have connected the cells within a tissue in vivo, which have been collected from an organ, tissue or fluid by any suitable method which results in the collection of a suitable number of cells for evaluation by the method of the present invention.

In some aspects, the sample can comprise blood. In still some aspects the sample can comprise whole blood, Peripheral Blood Mononuclear Cells (PBMCs), leukocytes, monocytes, lymphocytes, basophils, or eosinophils. In one aspect the blood sample comprises leukemia cells. In yet another aspect, the leukemia cells can be separated out from other cells and components in a blood sample.

The PCDH9 inhibitor can be selected from an antibody, an antisense molecule, an siRNA molecule, an shRNA molecule, a receptor antagonist, a chemical entity, a nucleotide, a peptide, and a protein. In a preferred aspect, the PCDH9 inhibitor is a PCDH9 antibody.

As used herein, the term "expression", when used in connection with detecting the expression of a gene, can refer to detecting transcription of the gene (i.e., detecting mRNA levels) and/or to detecting translation of the gene (detecting the protein produced). To detect expression of a gene refers to the act of actively determining whether a gene is expressed or not. This can include determining whether the gene expression is upregulated (or increased) as compared to a control, downregulated as compared to a control, or unchanged as compared to a control or increased or decreased as compared to a reference or control level. Therefore, the step of detecting or determining expression does not require that expression of the gene actually is upregulated or downregulated or increased or decreased, but rather, can also include detecting or determining that the expression of the gene has not changed (i.e., detecting no expression of the gene or no change in expression of the gene).

Expression of transcripts and/or proteins is measured by any of a variety of known methods in the art. For RNA expression, methods include but are not limited to: extraction of cellular mRNA and Northern blotting using labeled probes that hybridize to transcripts encoding all or part of the gene; amplification of mRNA using gene-specific primers, polymerase chain reaction (PCR), and reverse transcriptase-polymerase chain reaction (RT-PCR), quantitative PCR, and/or RNA Ampliseq, followed by quantitative detection of the product by any of a variety of means; multiplexed quantitative PCR enrichment of cDNA amplicons, followed by conversion of amplicons to sequence libraries and Next-generation based sequencing of libraries to generate digital count expression data; extraction of total RNA from the cells, which is then labeled and used to probe cDNAs or oligonucleotides encoding the gene on any of a variety of surfaces; in situ hybridization; and detection of a reporter gene.

Methods to measure protein expression levels generally include, but are not limited to: mass spectrometry, Western blot, immunoblot, enzyme-linked immunosorbant assay (ELISA), radioimmunoassay (MA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al., 1993, *Anal. Biochem.* 212:457; Schuster et al., 1993, *Nature* 365:343). Other suitable assays for measuring the binding of one protein to another include, for example, immunoassays such as enzyme linked immunoabsorbent assays (ELISA) and radioimmunoassays (MA); or determination of binding by monitoring the change in the spectroscopic or optical properties of the proteins through fluorescence, UV absorption, circular dichroism, or nuclear magnetic resonance (NMR).

In one aspect, the presence of PCDH9 expression is detected above a control threshold level or the expression level of PCDH9 is higher than the expression level of PCDH9 from a control. In one aspect, the expression can be at least about 5%, at least about 10%, at least about 20%, at least about 30%, at least about 40%, at least about 50%, at least about 60%, at least about 70%, at least about 80%, at least about 90%, higher than the expression level from the control. In still another aspect, the expression level can be at least about a 2 fold, at least about a 3 fold, at least about a 4 fold, at least about a 5 fold, at least about a 10-fold, at least about a 20 fold, at least about a 25 fold, at least about a 30 fold, at least about a 40 fold or at least about a 50 fold amount higher than the expression level from the control.

As used herein, reference to a reference or control means a subject who is a relevant reference or control to the subject being evaluated by the methods of the present invention. Such a relevant reference or control includes but is not limited to a subject or group of subjects having a hematological cancer such as leukemia or lymphoma, but have not relapsed over a determined time period. The reference or control expression level, such as the level used to determine the threshold level, used in the comparison of the methods of the present invention can be determined from one or more relevant reference or control subjects.

According to the methods of the present invention, a therapeutically effective amount of a PCDH9 inhibitor or a composition comprising a PCDH9 inhibitor that is administered to a subject, comprises an amount that is capable of inhibiting expression and/or activity of PCDH9 (mRNA and/or protein) without being toxic to the subject. An amount that is toxic to a subject comprises any amount that causes damage to the structure or function of a subject (i.e., poisonous). Further, the PCDH9 inhibitor can be used in combination with current ALL therapies. This approach is particularly valuable in reducing the need, duration, or intensity of CNS-directed therapies (intrathecal chemotherapy or cranial irradiation) which have deleterious side-effects, particularly in children.

The invention also provides for a kit for determining expression level of PCDH9. The kit can comprise one or more components selected from an antibody, an antisense RNA molecule, and a molecular probe or tag, wherein in the component can detect the expression of PCDH9.

In addition, according to the present invention, the composition as well as the kits of the present invention, can comprise a pharmaceutically acceptable excipient. According to the present invention, the PCDH9 inhibitor or composition comprising a PCDH9 inhibitor, can be administered with a pharmaceutically acceptable carrier, which includes pharmaceutically acceptable excipients and/or delivery vehicles, for delivering the agent to a subject (e.g., a liposome delivery vehicle). As used herein, a pharmaceutically acceptable carrier refers to any substance suitable for delivering a therapeutic composition useful in the method of the present invention to a suitable in vivo or ex vivo site. Preferred pharmaceutically acceptable carriers are capable of maintaining the composition of the present invention in a form that, upon arrival of the composition to a target cell, the composition is capable of entering the cell and inhibiting PCDH9 (mRNA and/or protein) in the cell. Further, as PCDH9 is a surface molecule, an anti-PCDH9 antibody can also inhibit PCDH9 on the surface of the cells without having to enter to the cells. Suitable excipients of the present invention include excipients or formularies that transport or help transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters, glycols and combinations thereof. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

Administration of a PCDH9 inhibitor or composition comprising a PCDH9 inhibitor can be systemic, mucosal and/or proximal to the location of the target site (e.g., near a site of a tumor). Suitable routes of administration will be apparent to those of skill in the art, depending on the type of cancer to be prevented or treated and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992).

In one aspect of the invention, one or more additional therapeutic agents or therapeutic protocols are administered or performed sequentially and/or concurrently with the administration of the PCDH9 inhibitor or composition comprising a PCDH9 inhibitor, e.g., administration of chemotherapy, administration of radiation therapy, administration of a tyrosine kinase inhibitor (TKI), administration of an immunotherapy composition or immunotherapy including include the additional administration of other agents, such as cytokines, antibodies, or other agents.

In one aspect, one or more therapies for cancer (including any therapies described herein or otherwise known in the art) can be administered or performed prior to, concurrently with, or after the administration of the PCDH9 inhibitor or composition comprising a PCDH9 inhibitor. In one embodiment, one or more therapies can be administered or performed in an alternating manner.

According to the methods of the present invention, the subject can be any animal subject, and particularly, in any vertebrate mammal, including, but not limited to, primates, rodents, livestock or domestic pets. Preferred mammals for the methods of the present invention are humans.

The following examples are provided for illustrative purposes and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

Figure 9:
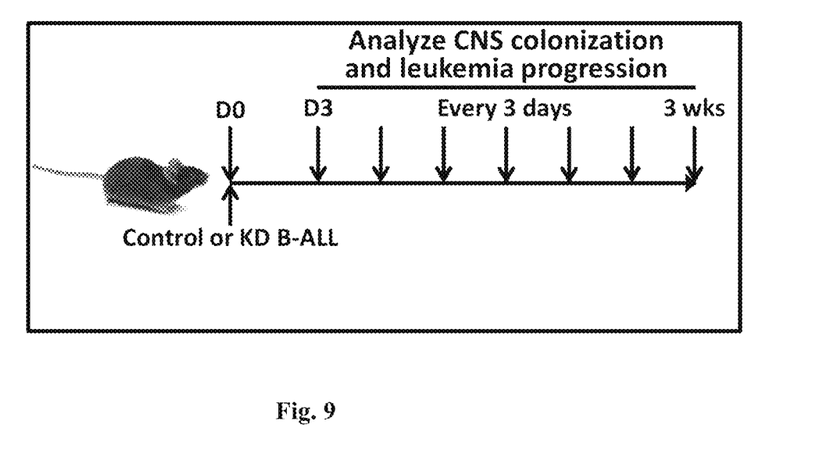
FIG. 9. shows a schematic for the setup for the long-term CNS colonization experiments discussed in the example section.

PCDH9 Depletion Reduces B-ALL Leukemia Colonization of the CNS:

Using a CNS B-ALL cell line, the ability of PCDH9-deficient leukemia cells to colonize the CNS in vivo is determined. For short-term assays (12, 24 and 48 hours post-transfer), $2\times10^7$ differentially fluorescently-labeled control and PCDH9 KD B-ALL cells, which express the congenic marker CD45.2, are intravenously (I.V.) co-transferred at a 1:1 ratio into CD45.1+C57BL/6 recipient mice. For long-term assays (every 3 days for up to 3 weeks) $5\times10^4$ control or PCDH9 KD B-ALL cells are transferred into separate cohorts of CD45.1+ recipient mice then, every 3 days, 2 randomly selected surviving mice from each cohort are euthanized for analysis (FIG. 9). By transferring $2\times10^7$ B-ALL cells, B-ALL cells infiltrating the CNS 24 hours post-transfer are detected and with $5\times10^4$ transferred B-ALL cells, disease progression over 2-3 weeks (Wigton, E. J., Thompson, S. B., Long, R. A. & Jacobelli, J. Myosin-IIA regulates leukemia engraftment and brain infiltration in a mouse model of acute lymphoblastic leukemia. *Journal of leukocyte biology* (2016)) is monitored. Mice given $5\times10^4$ transferred control B-ALL typically succumb to the leukemia within 21 days (Wigton, E. J., Thompson, S. B., Long, R. A. & Jacobelli, J. Myosin-IIA regulates leukemia engraftment and brain infiltration in a mouse model of acute lymphoblastic leukemia. *Journal of leukocyte biology* (2016)). Using flow cytometry the number and ratio of control and PCDH9 KD leukemia cells present in the CNS (brain and spinal cord) is quantified in a similar manner to techniques described in Wigton, E. J., et al. (in *Journal of leukocyte biology* (2016)). For comparison and to demonstrate that PCDH9 depletion does not affect leukemia colonization of other tissues, the number and ratio of transferred control vs. PCDH9 KD leukemia cells in the blood and other typical leukemia dissemination sites including: bone marrow, spleen, lymph nodes, liver, and lungs are also quantified. It is expected that PCDH9 depletion reduces B-ALL cell colonization of the CNS and other tissues over time.

Example 2

PCDH9 Depletion Reduces the Frequency of Leukemia-Induced CNS Pathology:

Following experiments with the CNS B-ALL cells as shown in FIG. 4, PCDH9-deficient leukemia cells are tested for reduced capacity to give rise to CNS pathology (paralysis of the recipient mice). The specificity of PCDH9 KD is confirmed using a second independent shRNA construct for PCDH9. Cohorts of 5 C57BL/6 recipient mice are injected I.V. with $5\times10^4$ control or PCDH9 KD B-ALL cells. Recipient mice are observed daily for up to 6 weeks and euthanized upon developing signs of morbidity (e.g. >20% weight loss, or a combination of 15-20% weight loss and any of the following: hunched posture, reduced activity, dehydration, respiratory distress, poor mobility, or ascending paralysis of the recipient mice—a sign of CNS infiltration by the leukemia). CNS pathology is scored on a scale of 0 to 5, and mice may be given in between scores (e.g. 0.5, 1.5, etc.) when the clinical picture lies between two defined scores. Scoring is as follows: normal motor functions of the mouse=0; limp tail=1; limp tail and partial hind limb paralysis=2; limp tail and full hind limb paralysis=3; limp tail, complete hind leg and partial front leg paralysis=4; complete paralysis=5. Mice typically do not score higher than 3 and any mouse with a score of 4 or higher will be immediately euthanized. It is expected that PCDH9 deficiency prevents or reduces the incidence and severity of leukemia-induced CNS pathology.

Example 3

Expression of PCDH9 Sufficient to Promote Leukemia CNS Colonization and Pathology:

Expression of PCDH9 in B-ALL leukemia cells is enforced in order to show if the expression is sufficient to promote CNS colonization and give rise to CNS pathology. Using retroviral transduction, the expression of PCDH9 is forced in the PCDH9-negative B-ALL cells that have a systemic phenotype. The time-course experiments discussed above are repeated to compare the capacity to colonize the CNS of control-transduced vs. PCDH9-transduced systemic B-ALL cells. The PCDH9-transduced systemic B-ALL cells give rise to CNS pathology compared to control-transduced B-ALL cells. It is expected that PCDH9 is sufficient to enable B-ALL cells to colonize the CNS and lead to CNS pathology.

Example 4

PCDH9 Regulates the Ability of Human ALL Cells to Colonize the CNS and Cause CNS Pathology:

This examples discusses if PCDH9 depletion inhibits the capacity of human B-ALL cells to colonize the CNS and give rise to CNS pathology. For these experiments, the human B-ALL cell line NALM-6 is used which gives rise to CNS pathology in a xenograft model[22]. $5\times10^6$ control or PCDH9 KO NALM-6 cells is I.V. transferred into cohorts of SCID mice. The ability of PCDH9-deficient NALM-6 cells (identified by staining for human CD19 and CD22) to colonize the CNS in vivo is determined using a time-course analysis every 7 days for 6 weeks and to cause CNS pathology over 12 weeks. It is expected that PCDH9 also plays a key role in enabling human ALL cells to colonize the CNS and cause CNS pathology.

The proliferation rate of control and PCDH9 KD B-ALL cells, and control and PCDH9 KO NALM-6 cells is determined. If any differences are determined in disease progression or survival rates due to better control of CNS colonization or differences in initial engraftment, the level of engraftment of control vs. PCDH9-depleted B-ALL and NALM-6 cells within 24 hours of transfer is analyzed. If reduced numbers are detected of PCDH9-depleted vs. control cells in the blood or bone marrow of recipient mice within 24 hours, leukemia progression experiments transferring more PCDH9-depleted B-ALL or NALM-6 cells are repeated to obtain similar initial levels of leukemia engraftment. Additionally, due to possible selective pressure against PCDH9 KD, the expression level of PCDH9 in KD B-ALL cells recovered from the CNS and other tissues during leukemia progression is determined. If shRNA-mediated depletion of PCDH9 in B-ALL cells is lost over time in vivo, stable genetic PCDH9 KO B-ALL cells are established using CRISPR/Cas9 technology (as for the NALM-6 cells).

Example 5

PCDH9 KD with TKI Treatment Improve Post-Treatment Survival in a B-ALL Transfer Model:

In this leukemia mouse model, in the absence of anti-leukemia treatment, CNS B-ALL cells transferred in immuno-competent non-irradiated mice typically results in overt leukemia and CNS pathology by 2-3 weeks post-transfer (FIG. 1 and Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011); Williams, R. T., Roussel, M. F. & Sherr, C. J. Arf gene loss enhances oncogenicity and limits imatinib response in mouse models of Bcr-Abl-induced acute lymphoblastic leukemia. *Proceedings of the National Academy of Sciences of the United States of America* 103, 6688-6693 (2006)). Cohorts of 5 C57BL/6 mice are injected I.V. with $5\times10^4$ control or PCDH9 KD B-ALL cells. Mouse cohorts are treated daily with vehicle or the TKI dasatinib (a second-generation Bcr-Abl inhibitor) typically used for treatment of Bcr-Abl+ ALL patients (Pui, C. H. & Evans, W. E. Treatment of acute lymphoblastic leukemia. *The New England journal of medicine* 354, 166-178 (2006)). Although dasatinib can slow leukemia progression in this mouse model of ALL it is still not able to effectively control CNS relapses (Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011)), as is often the case in human clinical settings (Ottmann, O. et al. Dasatinib induces rapid hematologic and cytogenetic responses in adult patients with Philadelphia chromosome positive acute lymphoblastic leukemia with resistance or intolerance to imatinib: interim results of a phase 2 study. *Blood* 110, 2309-2315 (2007)). Dasatinib or vehicle-only treatment starts 2 or 6 days post B-ALL transfer. This delayed TKI treatment allows the development of different degrees of leukemia burden and possible CNS dissemination prior to treatment and mimics common clinical settings in which human patients present with significant disease burden at diagnosis. Dasatinib treatment is suspended after 4 weeks and the mice are continued to be monitored for up to 12 weeks to determine the frequency of leukemia relapse and CNS pathology. Recipient mice are observed daily and euthanized upon developing signs of morbidity, while CNS pathology is determined by the development of ascending paralysis, which in this setting is a sign of CNS colonization by leukemia cells. It is expected that PCDH9 depletion in combination with the TKI dasatinib prevents or reduces the frequency of leukemia relapse and improve survival.

Example 6

The Combination of PCDH9 Depletion and Anti-Leukemia Treatment in a Human Xenograft Leukemia Model Prevent Relapses and Improve Survival:

Translatability of PCDH9 inhibition in the context of human leukemia, is determined using a xenograft leukemia model with human NALM-6 B-ALL cells, which give rise to CNS pathology (as described above). $5\times10^6$ control or PCDH9 KO NALM-6 cells is I.V. transferred into cohorts of 5 SCID mice and then treated daily for 4 weeks with vehicle or dexamethasone (a glucocorticoid chemotherapy agent used in the clinic that has efficacy on NALM-6 cells; administered in drinking water at 6 mg/L). Dexamethasone treatment is suspended after 4 weeks and the mice continue to be monitored for up to 12 weeks to determine the frequency of leukemia relapse and CNS pathology. It is expected that PCDH9 depletion in combination with chemotherapy prevents or reduces the frequency of leukemia relapse improving survival in human leukemia xenograft model.

Alternative treatment conditions such as the following can be used: (1) different regimens of dasatinib (including starting treatment at different days post B-ALL transfer or prolonging the treatment window); and (2) adding a chemotherapy treatment such as dexamethasone (which has efficacy on this B-ALL cell line (Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011))) to the dasatinib treatment. Similarly, in the case of the NALM-6 xenograft model alternative chemotherapy regimens and treatments can be used. NALM-6 cells are not Bcr-Abl+ therefore dasatinib TKI treatment is not a viable option.

PCDH9 blocking antibodies can have therapeutic efficacy in limiting leukemia CNS relapses without significant side-effects. To prevent leukemia relapses in the CNS, particularly if PCDH9 antibodies have undesirable side-effects, targeted carriers (such as B cell-directed antibodies or nanoparticles (Davis, M. E. et al. Evidence of RNAi in humans from systemically administered siRNA via targeted nanoparticles. *Nature* 464, 1067-1070 (2010); Kim, S. S., Subramanya, S., Peer, D., Shimaoka, M. & Shankar, P. Antibody-mediated delivery of siRNAs for anti-HIV therapy. *Methods Mol Biol* 721, 339-353 (2011); Peer, D., Park, E. J., Morishita, Y., Carman, C. V. & Shimaoka, M. Systemic leukocyte-directed siRNA delivery revealing cyclin D1 as an anti-inflammatory target. *Science* 319, 627-630 (2008)) loaded with PCDH9-specific interfering-RNA for delivery to leukemia cells are used. This allows selective targeting of leukemia cells, or only a particular leukocyte subset (such as B cells), thus minimizing possible unwanted effects of more generalized PCDH9 inhibition.

Primary human leukemia xenografts into NSG (NOD SCID Gamma) mice are analyzed to confirm the efficacy of PCDH9 KD on a range of primary leukemias derived from pediatric patients. It is expected that PCDH9 depletion in primary human leukemia cells will also prevent or reduce CNS colonization in these xenograft models.

In the examples above, focus is on models of ALL, although the data obtained is relevant to any leukemia that uses ectopic PCDH9 expression as a means to invade and colonize the CNS. This further broadens the benefits of PCDH9 inhibition, including in combination therapies.

While various embodiments of the present invention have been described in detail, it is apparent that modifications and adaptations of those embodiments will occur to those skilled in the art. It is to be expressly understood, however, that such modifications and adaptations are within the scope of the present invention.

REFERENCES

1. Pfeifer, H. et al. Risk and prognosis of central nervous system leukemia in patients with Philadelphia chromosome-positive acute leukemias treated with imatinib mesylate. *Clinical cancer research: an official journal of the American Association for Cancer Research* 9, 4674-4681 (2003).

2. Leis, J. F. et al. Central nervous system failure in patients with chronic myelogenous leukemia lymphoid blast crisis and Philadelphia chromosome positive acute lymphoblastic leukemia treated with imatinib (STI-571). *Leukemia & lymphoma* 45, 695-698 (2004).
3. Pui, C. H. & Thiel, E. Central nervous system disease in hematologic malignancies: historical perspective and practical applications. *Seminars in oncology* 36, S2-S16 (2009).
4. Aragon-Ching, J. B. & Zujewski, J. A. CNS metastasis: an old problem in a new guise. *Clinical cancer research: an official journal of the American Association for Cancer Research* 13, 1644-1647 (2007).
5. Wolff, N.C., Richardson, J. A., Egorin, M. & Ilaria, R. L., Jr. The CNS is a sanctuary for leukemic cells in mice receiving imatinib mesylate for Bcr/Abl-induced leukemia. *Blood* 101, 5010-5013 (2003).
6. Pui, C.-H. & Howard, S. C. Current management and challenges of malignant disease in the CNS in paediatric leukaemia. *The Lancet Oncology* 9, 257-268 (2008).
7. Espy, K. A. et al. Chemotherapeutic CNS prophylaxis and neuropsychologic change in children with acute lymphoblastic leukemia: a prospective study. *Journal of pediatric psychology* 26, 1-9 (2001).
8. Goshen, Y. et al. High incidence of meningioma in cranial irradiated survivors of childhood acute lymphoblastic leukemia. *Pediatric blood & cancer* 49, 294-297 (2007).
9. Shuper, A. et al. Methotrexate treatment protocols and the central nervous system: significant cure with significant neurotoxicity. *Journal of child neurology* 15, 573-580 (2000).
10. Strehl, S., Glatt, K., Liu, Q. M., Glatt, H. & Lalande, M. Characterization of two novel protocadherins (PCDH8 and PCDH9) localized on human chromosome 13 and mouse chromosome 14. *Genomics* 53, 81-89 (1998).
11. Silveira, V. S. et al. Gene expression pattern contributing to prognostic factors in childhood acute lymphoblastic leukemia. *Leukemia & lymphoma* 54, 310-314 (2013).
12. Moore, I. M. et al. Cognitive consequences and central nervous system injury following treatment for childhood leukemia. *Seminars in oncology nursing* 16, 279-290; discussion 291-279 (2000).
13. Wigton, E. J., Thompson, S. B., Long, R. A. & Jacobelli, J. Myosin-IIA regulates leukemia engraftment and brain infiltration in a mouse model of acute lymphoblastic leukemia. *Journal of leukocyte biology* (2016).
14. Jacobelli, J., Estin Matthews, M., Chen, S. & Krummel, M. F. Activated T Cell Trans-Endothelial Migration Relies on Myosin-IIA Contractility for Squeezing the Cell Nucleus through Endothelial Cell Barriers. *PLoS one* 8, e75151 (2013).
15. Jacobelli, J. et al. Confinement-optimized three-dimensional T cell amoeboid motility is modulated via myosin IIA-regulated adhesions. *Nature immunology* 11, 953-961 (2010).
16. Wang, C. et al. Downregulation of PCDH9 predicts prognosis for patients with glioma. *Journal of clinical neuroscience: official journal of the Neurosurgical Society of Australasia* 19, 541-545 (2012).
17. Wang, C. et al. Characterizing the role of PCDH9 in the regulation of glioma cell apoptosis and invasion. *Journal of molecular neuroscience: MN* 52, 250-260 (2014).
18. Boulos, N. et al. Chemotherapeutic agents circumvent emergence of dasatinib-resistant BCR-ABL kinase mutations in a precise mouse model of Philadelphia chromosome-positive acute lymphoblastic leukemia. *Blood* 117, 3585-3595 (2011).
19. Williams, R. T., Roussel, M. F. & Sherr, C. J. Arf gene loss enhances oncogenicity and limits imatinib response in mouse models of Bcr-Abl-induced acute lymphoblastic leukemia. *Proceedings of the National Academy of Sciences of the United States of America* 103, 6688-6693 (2006).
20. Williams, R. T., den Besten, W. & Sherr, C. J. Cytokine-dependent imatinib resistance in mouse BCR-ABL+, Arf-null lymphoblastic leukemia. *Genes & development* 21, 2283-2287 (2007).
21. Jacoby, E., Chien, C. D. & Fry, T. J. Murine models of acute leukemia: important tools in current pediatric leukemia research. *Frontiers in oncology* 4, 95 (2014).
22. Gunther, R. et al. Biotherapy for xenografted human central nervous system leukemia in mice with severe combined immunodeficiency using B43 (anti-CD19)-pokeweed antiviral protein immunotoxin. *Blood* 85, 2537-2545 (1995).
23. Jacobelli, J., Bennett, F. C., Pandurangi, P., Tooley, A. J. & Krummel, M. F. Myosin-IIA and ICAM-1 regulate the interchange between two distinct modes of T cell migration. *J Immunol* 182, 2041-2050 (2009).
24. Pui, C. H. & Evans, W. E. Treatment of acute lymphoblastic leukemia. *The New England journal of medicine* 354, 166-178 (2006).
25. Ottmann, O. et al. Dasatinib induces rapid hematologic and cytogenetic responses in adult patients with Philadelphia chromosome positive acute lymphoblastic leukemia with resistance or intolerance to imatinib: interim results of a phase 2 study. *Blood* 110, 2309-2315 (2007).
26. Hu, Y. et al. Targeting multiple kinase pathways in leukemic progenitors and stem cells is essential for improved treatment of Ph+ leukemia in mice. *Proceedings of the National Academy of Sciences of the United States of America* 103, 16870-16875 (2006).
27. Davis, M. E. et al. Evidence of RNAi in humans from systemically administered siRNA via targeted nanoparticles. *Nature* 464, 1067-1070 (2010).
28. Kim, S. S., Subramanya, S., Peer, D., Shimaoka, M. & Shankar, P. Antibody-mediated delivery of siRNAs for anti-HIV therapy. *Methods Mol Biol* 721, 339-353 (2011).
29. Peer, D., Park, E. J., Morishita, Y., Carman, C. V. & Shimaoka, M. Systemic leukocyte-directed siRNA delivery revealing cyclin D1 as an anti-inflammatory target. *Science* 319, 627-630 (2008).

What is claimed:

1. A method of treating cancer comprising administering to a subject in need thereof, a Protocadherin-9 (PCDH9) inhibitor, wherein the cancer is leukemia or lymphoma and wherein the PCDH9 inhibitor is selected from the group consisting of an antisense molecule, an siRNA molecule, and an shRNA molecule.

2. The method of claim 1, wherein the leukemia is Acute Lymphoblastic Leukemia (ALL) or Acute Myeloid Leukemia (AML).

3. The method of claim 1, wherein the subject is further administered a systemic therapy selected from the group consisting of chemotherapy, radiation, and tyrosine kinase inhibitor (TKI) therapy.

4. The method of claim 1, wherein the subject is human.

5. A method to identify a subject at risk for leukemia cell colonization of the central nervous system (CNS) in a subject having leukemia, the method comprising:
   a. obtaining a blood sample from the subject;
   b. detecting the expression level of PCDH9 in the sample;
   c. identifying the subject as at risk for leukemia cell colonization of the CNS when either the presence of PCDH9 expression is detected above a control threshold level or the expression level of PCDH9 in the sample is higher than the expression level of PCHD9 from a control; and d. administering a PCDH9 inhibitor to the subject identified as being at risk, wherein the PCDH9 inhibitor is selected from the group consisting of an antisense molecule, an siRNA molecule, and an shRNA molecule.

6. The method of claim 5, wherein the subject is further administered a systemic therapy selected from the group consisting of chemotherapy, radiation, and tyrosine kinase inhibitor (TKI) therapy.

7. A method to reduce leukemia relapse in a subject, comprising:

a. obtaining a blood sample from the subject;
b. detecting the expression level of PCDH9 in the sample;
c. identifying the subject as at risk for leukemia relapse when either the presence of PCDH9 expression is detected above a control threshold level or the expression level of PCDH9 in the sample is higher than the expression level of PCHD9 from a control; and
d. administering a PCDH9 inhibitor to the subject at risk, wherein the PCDH9 inhibitor is selected from the group consisting of an antisense molecule, an siRNA molecule, and an shRNA molecule.

8. The method of claim 7, wherein the subject is further administered a systemic therapy selected from the group consisting of chemotherapy, radiation, and tyrosine kinase inhibitor (TKI) therapy.

9. A method to inhibit or reverse leukemia cell colonization of the CNS in a subject comprising:

a. obtaining a blood sample from the subject;
b. detecting the expression level of PCDH9 in the sample;
c. identifying the subject as at risk for leukemia cell colonization of the CNS when either the presence of PCDH9 expression is detected above a control threshold level or the expression level of PCDH9 in the sample is higher than the expression level of PCHD9 from a control; and
d. administering a PCDH9 inhibitor to the subject, wherein the PCDH9 inhibitor is selected from the group consisting of an antisense molecule, an siRNA molecule and an shRNA molecule.

10. The method of claim 9, wherein the subject is further administered a systemic therapy selected from the group consisting of chemotherapy, radiation, and tyrosine kinase inhibitor (TKI) therapy.

* * * * *